(12) United States Patent
Choi et al.

(10) Patent No.: US 9,655,577 B2
(45) Date of Patent: May 23, 2017

(54) APPARATUS AND METHOD FOR DIAGNOSING LESIONS

(75) Inventors: Jae Gu Choi, Ansan-si (KR); Young Wook Choi, Anyang-si (KR); Young Huh, Gunpo-si (KR)

(73) Assignee: Korea Electrotechnology Research Institute, Gyeongsangnam-do (KR)

( * ) Notice: Subject to any disclaimer, the term of this patent is extended or adjusted under 35 U.S.C. 154(b) by 538 days.

(21) Appl. No.: 13/980,464

(22) PCT Filed: Sep. 23, 2011

(86) PCT No.: PCT/KR2011/007015
§ 371 (c)(1),
(2), (4) Date: Oct. 11, 2013

(87) PCT Pub. No.: WO2012/099314
PCT Pub. Date: Jul. 26, 2012

(65) Prior Publication Data
US 2014/0037051 A1   Feb. 6, 2014

(30) Foreign Application Priority Data

Jan. 19, 2011 (KR) ........................ 10-2011-0005286

(51) Int. Cl.
*A61N 5/10* (2006.01)
*A61B 6/03* (2006.01)
(Continued)

(52) U.S. Cl.
CPC ............ *A61B 6/502* (2013.01); *A61B 6/4291* (2013.01); *A61B 6/5211* (2013.01); *A61B 6/582* (2013.01);
(Continued)

(58) Field of Classification Search
CPC ...... A61N 5/10; A61N 5/1048; A61N 5/1075; A61N 5/1077; A61N 5/1081; A61N 2005/1076; A61B 6/00; A61B 6/02; A61B 6/03; A61B 6/032; A61B 6/035; A61B 6/40; A61B 6/4021; A61B 6/4294; A61B 6/48; A61B 6/50; A61B 6/502; A61B 6/5211; A61B 6/54; A61B 6/58; A61B 6/582–6/584; A61B 6/589
See application file for complete search history.

(56) References Cited

U.S. PATENT DOCUMENTS 7,221,737 B2   5/2007  Hoheisel et al.
7,332,729 B1 *  2/2008  Muray et al. .......... B82Y 10/00
                                                        250/491.1
(Continued)

FOREIGN PATENT DOCUMENTS

JP    200862058 A     3/2008
JP    2008104673 A    5/2008
(Continued)

*Primary Examiner* — Anastasia Midkiff
(74) *Attorney, Agent, or Firm* — The Webb Law Firm

(57) ABSTRACT

Disclosed is an apparatus and a method for diagnosing lesions. More specifically, the present invention relates to an apparatus and a method for diagnosing lesions capable of precisely diagnosing lesions such as breast cancer by digital breast tomosynthesis (DBT). The present invention enables the improvement of lesion diagnosis accuracy and early diagnosis rates.

8 Claims, 17 Drawing Sheets

(51) Int. Cl.
*A61B 6/00* (2006.01)
*A61B 6/02* (2006.01)
*A61B 6/04* (2006.01)

(52) U.S. Cl.
CPC .............. *A61B 6/583* (2013.01); *A61B 6/584* (2013.01); *A61B 6/589* (2013.01); *A61N 5/1075* (2013.01); *A61B 6/025* (2013.01); *A61B 6/0414* (2013.01); *A61B 6/4452* (2013.01); *A61B 6/465* (2013.01); *A61B 6/587* (2013.01); *A61N 5/1081* (2013.01); *A61N 2005/1076* (2013.01)

(56) References Cited

U.S. PATENT DOCUMENTS

| | | | |
|---|---|---|---|
| 7,453,979 B2 * | 11/2008 | Sendai | A61B 6/025 378/23 |
| 7,697,661 B2 | 4/2010 | Souchay et al. | |
| 2006/0115054 A1 * | 6/2006 | Yatsenko et al. | A61B 5/06 378/207 |
| 2008/0056441 A1 * | 3/2008 | Souchay et al. | A61B 6/025 378/37 |
| 2011/0135053 A1 * | 6/2011 | Noordhoek et al. | A61B 6/583 378/11 |

FOREIGN PATENT DOCUMENTS

| | | |
|---|---|---|
| KR | 1020060008323 A | 1/2006 |
| WO | 2004105050 A1 | 12/2004 |
| WO | 2010028208 A1 | 3/2010 |

* cited by examiner (a)

(b)

(a)

(b)

(a)　　　　　　　　　　　　　(b)

(a)                          (b)

(a)                          (b)

APPARATUS AND METHOD FOR DIAGNOSING LESIONS

CROSS-REFERENCE TO RELATED APPLICATIONS

This application is the United States national phase under 35 U.S.C. §371 of International Application No. PCT/KR2011/007015 filed Sep. 23, 2011, entitled "Apparatus and Method for Diagnosing Lesions" and claims priority under 35 U.S.C. §119(a)-(d) to Korean Patent Application No. 10-2011-0005286, filed on Jan. 19, 2011 in the German Intellectual Property Office, the disclosures of which are hereby incorporated by reference in their entireties.

TECHNICAL FIELD

The present invention relates to an apparatus and a method for diagnosing lesions. More specifically, the present invention relates to an apparatus and a method for diagnosing lesions capable of accurately diagnosing lesions such as breast cancer by digital breast tomosynthesis (DBT).

BACKGROUND ART

With the recent advent of the aging era and the improvement of people's living standards, there is a tendency that a concern about an early diagnosis and a treatment of diseases for enjoying a healthy life gradually has increased and cancer among various diseases has become the most important cause of threatening people's health as the first place of a cause of Korean people's death.

According to the Cancer Registration Headquarter, part of the Ministry for Health, Welfare and Family Affairs, it is estimated that approximately 130,000 or more new cancer patients occur every year in Korean and the incidence rate thereof obtained by using the number of cancer occurrence cases registered from 2003 to 2005 reaches 300.0 cases for a male and 248.2 cases for a female per population of 100,000.

Further, in the case of dividing the occurred cancers in accordance with types thereof, occurrence rate is high in the order of stomach cancer, lung cancer, liver cancer, and colorectal cancer which occupy 66% in total occurred cancer in the case of males, while breast cancer is the higher in cancer occurrence rate than four main cancers in the order of the breast cancer, thyroid cancer, the stomach cancer, the colorectal cancer, and the lung cancer in the case of females.

As such, in the case of the female, early diagnosing and treating the breast cancer which is highest in occurrence rate is considered as an important factor which should be preceded so as for the female to enjoy a healthy life.

However, in the case of mammography mainly used for diagnosing the breast cancer for an asymptomatic female among breast cancer diagnosing methods, since a photographing result using an X-ray is a 2D image, a lesion of an interest region overlaps with a normal tissue, and as a result, it is difficult to detect micro-calcification which is an important factor in early diagnosis of the breast cancer.

Further, since a difference in X-ray absorption rate in a breast tissue and cancer is very small, a distinguishing capability is low, and as a result, there is a high possibility that breast false positive or breast false negative result will occur and actually, a diagnosis probability of the breast false positive result reaches 30% in a medical diagnosis field.

In particular, in the case of the breast false negative result that judges the person to be diagnosed as normal or positive even though the person to be diagnosed has the breast cancer, a patient is wrongly set at ease by disregarding the breast cancer and a mistake in which the breast cancer is late diagnosed is made, and as a result, the breast false negative serves as a main factor that threatens patient's health and causes a legal problem in view of a medical malpractice Accordingly, development of a breast cancer diagnosing method having high accuracy is significantly required to prevent additional examinations such as unnecessary rephotographing and biopsy by reducing a probability of the false positive result and the false negative result in diagnosing the breast cancer.

DISCLOSURE

Technical Problem

The present invention is contrived to solve the aforementioned problems and a subject of the present invention is to provide an apparatus and a method for diagnosing lesions capable of precisely diagnosing a lesion such as breast cancer while minimizing X-ray radiation exposure of a person to be diagnosed by digital breast tomosynthesis (DBT).

Technical Solution

In order to achieve the object, the apparatus for diagnosing lesions according to the present invention includes: an X-ray source generating X-rays to be irradiated to a subject; a subject support spaced apart from the X-ray source and in which the subject is positioned on an upper portion; a X-ray detector coupled to the lower portion of the subject support and generating 2D images with respect to the subject from the X-rays passing through the subject; and a lesion determination unit combining the 2D images to generate a 3D image with respect to the subject and determining the presence or absence of a lesion of the subject by using the 3D image, and the X-ray source rotates intermittently or continuously in accordance with a preset angle range and the generated X-rays is irradiated to the subject only when the X-ray source stops at a preset angleduring intermittent rotation, or the generated X-rays is irradiated to the subject at a preset angle during continuous rotation, and the X-ray detector generates projected images with respect to the subject generated in a plurality of locations by the X-rays passing through the subject in accordance with the rotation as the 2D images.

Further, a method for diagnosing lesions according to the present invention includes: (a) generating, by an X-ray source, X-rays to be irradiated to a subject; (b) generating 2D images with respect to the subject from the X-rays passing through the subject; (c) combining the 2D images to generate a 3D image with respect to the subject; and (d) determining the presence or absence of a lesion of the diagnosis subject by using the 3D image, and in step (a), the X-ray source rotates intermittently or continuously in accordance with a preset angle range and the generated X-ray is irradiated to the subject only when the X-ray source stops at a preset angle during intermittent rotation or the generated X-ray is irradiated to the subject at a preset angle during continuous rotation.

Advantageous Effects

According to the present invention, since a 3D image of a subject such as breasts, or the like is generated and thereafter, a lesion such as breast cancer can be diagnosed without overlapping of images by using the generated 3D image, accuracy of lesion diagnosis and early diagnosis rates can be improved.

Further, since an X-ray source rotates intermittently or continuously at high speed, and an X-ray is irradiated to the subject only when the X-ray source stops at a preset angle during intermittent rotation or the X-ray source is positioned at a specific angle during continuous rotation, X-ray radiation exposure to a person to be diagnosed can be minimized.

BEST MODE

Figure 1:
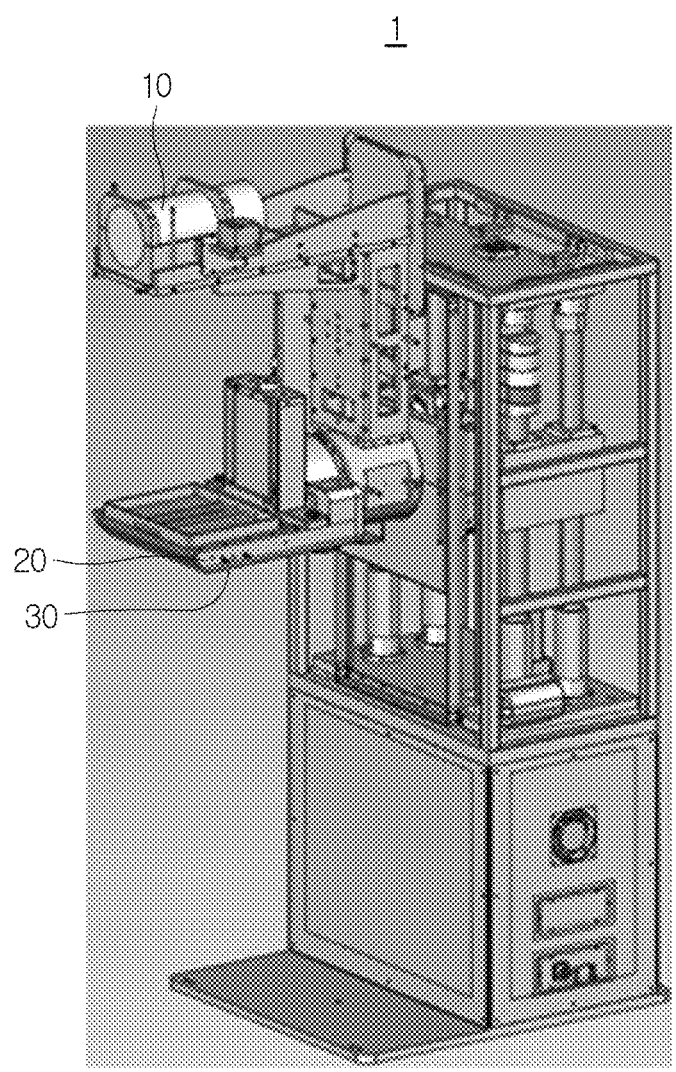
FIG. 1 is a perspective view of an apparatus for diagnosing lesions according to an exemplary embodiment of the present invention.

Exemplary embodiments of the present invention will be described in detail with reference to the accompanying drawings. First, when reference numerals refer to components of each drawing, it is noted that although the same components are illustrated in different drawings, the same components are referred to by the same reference numerals as possible. In describing the present invention, when it is determined that the detailed description of the known art related to the present invention may obscure the gist of the present invention, the detailed description thereof will be omitted. Further, hereinafter, the exemplary embodiments of the present invention will be described, but the spirit of the present invention is not limited or restricted thereto and can, of course, be implemented by those skilled in the art.

Figure 2:
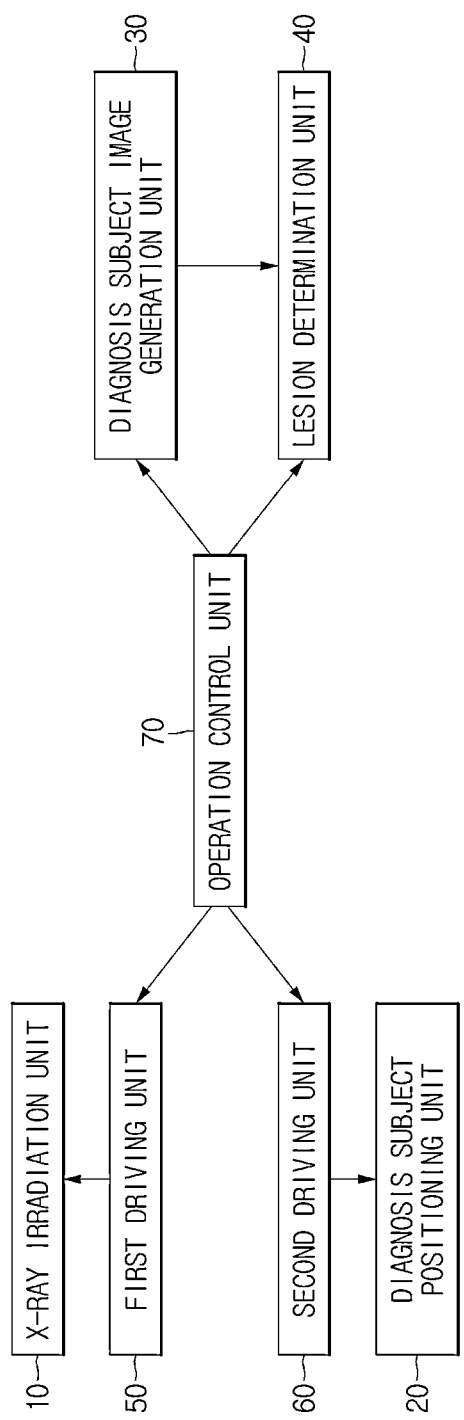
FIG. 2 is a control block diagram of the apparatus for diagnosing lesions according to the exemplary embodiment of the present invention.

FIG. 1 is a perspective view of an apparatus for diagnosing lesions according to an exemplary embodiment of the present invention. FIG. 2 is a control block diagram of the apparatus for diagnosing lesions according to the exemplary embodiment of the present invention.

As illustrated in FIGS. 1 and 2, an apparatus 1 for diagnosing lesions according to the exemplary embodiment of the present invention includes an X-ray source 10, a subject support 20, an X-ray detector 30, a lesion determination unit 40, a first driving unit 50, a second driving unit 60, and an operation control unit 70.

The X-ray source 10 generates X-rays and the generated X-rays are irradiated to a subject.

In this case, the X-ray source 10 may be an X-ray tube and the X-ray source 10 rotates intermittently or continuously in accordance with a preset angle range and the generated X-ray may be irradiated the subject at a preset angle during intermittently or continuously rotation.

In this case, the preset angle range which is an intermittent or continuous rotation range of the X-ray source 10 may be −20 degrees to 20 degrees.

The subject support 20 is spaced apart from the X-ray source 10 and is configured to match the X-ray source 10 at their central axes, and as a result, a focus of the generated X-rays may be positioned at the center of the subject support 20 and the subject is placed on the upper portion of the subject support 20.

In this case, the subject may be a breast of a person to be diagnosed, and although not illustrated, the apparatus 1 for diagnosing lesions may further include a fixation plate that is positioned in the upper part of the subject to fix the subject.

The X-ray detector 30 is coupled to the lower portion of the subject support 20 and generates 2D images with respect to the subject from the X-rays passing through the subject.

In this case, the X-ray detector 30 may be a digital type semiconductor flat panel detector, and in the semiconductor flat panel detector, a plurality of sensors is configured in a matrix pattern to have advantages such as higher resolution, a wider dynamic ranges, generation of higher electrical signals, and easier data processing than a film used in the related art.

Accordingly, the 2D images may be processed and reproduced in real time and the 2D images having high resolution may be acquired from a comparatively small amount of X-ray.

Further, the 2D images may be a plurality of projected images with respect to a subject generated in a plurality of locations by the X-rays passing through the subject after being irradiated to the subject from the X-ray source 10.

The lesion determination unit 40 combines the 2D images image transmitted from the X-ray detector 30 to generate a 3D image with respect to the subject and determine the presence or absence of a lesion (for example, breast cancer) of the subject from the 3D image.

For example, when the lesion determination unit 40 determines that an image having a specific size and specific luminance is included in the 3D image, the lesion determination unit 40 may recognize the presence or absence of the breast cancer of the subject by determining that the corresponding image is the lesion.

The first driving unit 50 rotates the X-ray source 10 in accordance with a preset angle range and the second driving unit 60 rotates the subject support 20 in accordance with a preset angle range.

In this case, detailed configurations of the first driving unit 50 and the second driving unit 60 will be described below with reference to FIG. 3.

The operation control unit 70 controls operations of the X-ray source 10, the X-ray detector 30, the lesion determination unit 40, the first driving unit 50, and the second driving unit 60.

In this case, a detailed operation control process of the operation control unit 70 will be described below with reference to FIGS. 3, 9, and 10.

Figure 3:
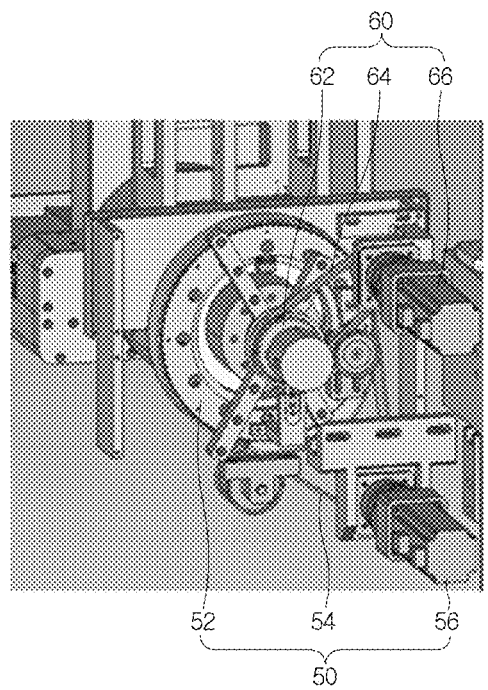
FIG. 3 is a partially enlarged diagram of a first driving unit and a second driving unit of FIG. 2.

FIG. 3 is a partially enlarged diagram of the first driving unit 50 and the second driving unit 60 of FIG. 2.

As illustrated in FIG. 3, the first driving unit 50 includes a first rotation gear 52, a first driving belt 54, and a first driving pulley 56 and the second driving unit 60 includes a second rotation gear 62, a second driving belt 64, and a second driving pulley 66.

In this case, the first driving pulley 56 and the second driving pulley 66 may further include a motor for generating driving force and a deceleration gear which is connected with a rotation shaft of the motor and capable of reducing vibration generated from the motor by controlling the driving force generated from the motor.

Further, in the case of the first driving unit 50, when the first driving pulley 56 is electrically driven by control by the operation control unit 70, the driving force of the first driving pulley 56 is transferred to the first rotation gear 52 through the first driving belt 54 to rotate the first rotation gear 52, and as a result, the X-ray source 10 coupled to the first rotation gear 54 may be rotated within a preset angle range and a rotational speed of the X-ray source 10 by the operation of the first driving unit 50 may be in the range of 3°/sec to 5°/sec (approximately 4.3°/sec).

The rotation speed range of the X-ray source 10 presented as above is a value presented as a rotational speed range in which X-ray irradiation to the subject may be completed while a breath of the person to be diagnosed is not instable by considering −20 degrees to 20 degrees which is the rotation angle range of the X-ray source 10.

Further, in the case of the first driving unit 50, since the driving force generated from the motor of the first driving pulley 56 is controlled by the deceleration gear and thereafter, transferred to the first rotation gear 52 through the first driving belt 54 to rotate the first rotation gear 52, the vibration which is generated during the rotation of the X-ray source 10 may be reduced.

In addition, in the case of the second driving unit 60, when the second driving pulley 66 is electrically driven by the control by the operation control unit 70, the driving force generated from the motor of the second driving pulley 66 is transferred to the second rotation gear 62 through the second driving belt 64 to rotate the second rotation gear 62, and as a result, the subject support 20 coupled to the second rotation gear 62 may be rotated in a preset angle range (−90 degrees to 90 degrees).

Further, in the case of the second driving unit 60, since the driving force generated from the motor of the second driving pulley 66 is controlled by the deceleration gear and thereafter, transferred to the first rotation gear 62 through the second driving belt 64 to rotate the first rotation gear 62, the vibration which is generated during the rotation of the diagnosis subject positioning unit 20 may be reduced.

As such, in the case of the apparatus 1 for diagnosing lesions according to the exemplary embodiment of the present invention, the first driving unit 50 for intermittently or continuously rotating the X-ray source 10 within a preset angle range and the second driving unit 60 for rotating the subject support 20 within a preset angle range are separately configured by the control by the operation control unit 70 to respectively rotate the X-ray source 10 and the subject support 20, thereby enabling the X-ray source 10 and the subject support 20 to be rapidly and precisely rotated.

Accordingly, since focus calibration of the X-ray irradiated from the X-ray source 10 or position calibration of the subject support 20 may be easily achieved, generation of the 2D images with a minimized error, which is capable of improving accuracy of diagnosing a lesion of the person to be diagnosed is enabled.

Figure 4:
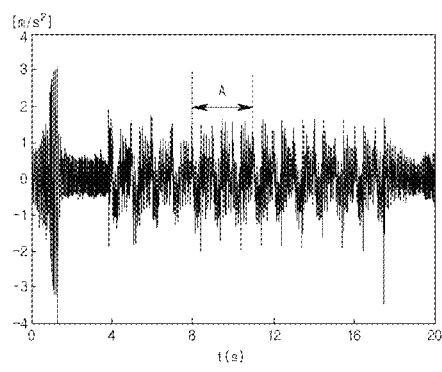
FIG. 4 is a graph for referring to a vibration characteristic of an X-ray source of FIG. 1.
Figure 4:
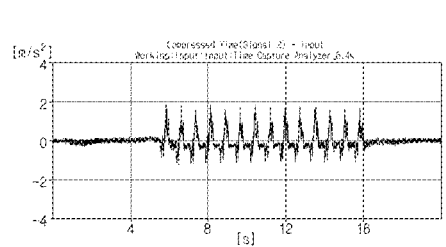

FIG. 4 is a graph for referring to a vibration characteristic of an X-ray source of FIG. 1.

As illustrated in FIG. 4, when a vibration characteristic (FIG. 4(*a*)) of an X-ray source of a conventional product and a vibration characteristic (FIG. 4(*b*)) of the X-ray source 10 are compared with each other, it can be seen that the vibration characteristic of the X-ray source 10 is more excellent (vibration of the X-ray source 10 is reduced).

As such, in the case of the apparatus 1 for diagnosing lesions according to the exemplary embodiment of the present invention, the first pulley 56 and the second pulley 66 that generate the driving force of the first driving unit 50 and the second driving unit 60 are configured by combining the motor and the deceleration gear, and the X-ray source 10 and the subject support 20 are rotated by rotation of the first rotation gear 52 and the second rotation gear 62, and as a result, vibration characteristics and mechanical driving characteristics of the X-ray source 10 and the subject support 20 may be improved.

Accordingly, since vibration of the focus of the X-ray irradiated from the X-ray source 10 to the subject is reduced to prevent the resolution of the 2D images generated by the X-ray detector 30 from being degraded and reduce vibrations of the X-ray source 10 and the subject support 20, total vibration is reduced, thereby improving durability of the apparatus 1 for diagnosing lesions and increasing a life-span thereof.

Further, hereinafter, an operating process of the apparatus 1 for diagnosing lesions according to the exemplary embodiment of the present invention will be described in detail with reference to FIGS. 5 to 8.

FIGS. 5 to 8 are operation reference diagrams of the apparatus for diagnosing lesions according to the exemplary embodiment of the present invention.

Figure 5:
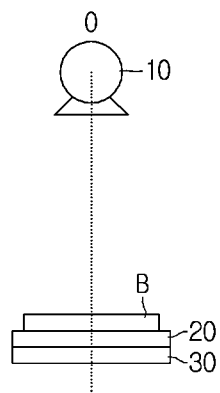
FIGS. 5 to 8 are operation reference diagrams of the apparatus for diagnosing lesions according to the exemplary embodiment of the present invention.

Prior to the operation of the apparatus 1 for diagnosing lesions according to the exemplary embodiment of the present invention, as illustrated in FIG. 5, the X-ray source 10, the subject support 20 vertically spaced from the X-ray source 10, a subject B positioned on the upper portion of the subject support 2Q, and the X-ray detector 30 coupled to the lower portion of the subject support 20 may share a same center axis.

As such, the reason for sharing the same center axis of the X-ray source 10, the subject B, the subject support 20, and the X-ray detector 30 each other is that the focus of the X-ray irradiated from the X-ray source 10 to the subject B matches the center of the subject support 20 to generate the 2D images generated by the X-ray detector 30 without an error.

Further, prior to the operation of the apparatus 1 for diagnosing lesions, the focus calibration of the X-ray irradiated from the X-ray source 10 to the subject B may be achieved by controlling an angle of the X-ray source 10 or the subject support 20, and a detailed process of the X-ray focus calibration will be below described with reference to FIGS. 13 to 17.

Figure 6:
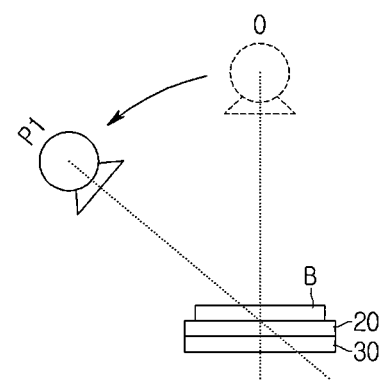
Figure 7:
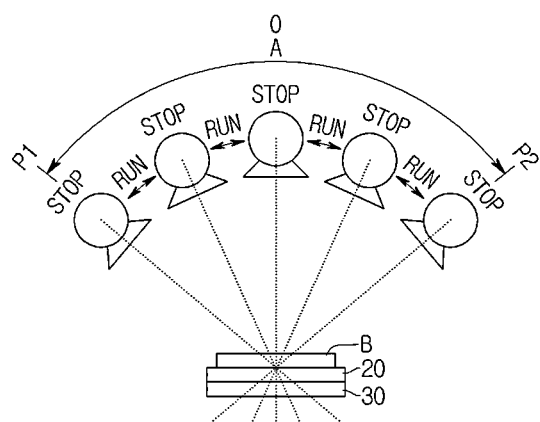

As illustrated in FIG. 6, for the operation of the apparatus 1 for diagnosing lesions, the X-ray source 10 is transported from an initial location O to one point P1 in accordance with a preset angle range and as illustrated in FIG. 7, the X-ray source 10 positioned at one point P1 is rotated to the other point P2 in accordance with a preset angle range A.

In this case, the preset angle range A, that is, an angle range from one point P1 to the other point P2 may be −20 degrees (an angle from the initial position O to one point P1) to 20 degrees (an angle from the initial position O to the other point p2) based on the initial position O of the X-ray source 10 and more preferably, −7.5 degrees to 7.5 degrees.

Further, it is possible to adjust the preset angle range in the operation control unit 70 in accordance with the width of the subject B.

As illustrated in FIG. 7, rotation of the X-ray source 10, which is performed from one point P1 to the other point P2 may be intermittent rotation in which a stop and a run are repeatedly performed and the generated X-rays is irradiated from the X-ray source 10 to the subject B only when the X-ray source 10 stops during intermittent rotation.

In this case, the number of times when the X-ray source 10 stops may be determined depending on the number of X-ray irradiation times which is preset in the operation control unit 70.

Further, although not illustrated in the figure, the rotation of the X-ray source 10, which is performed from one point P1 to the other point P2 may be the continuous rotation, and the generated X-rays may be irradiated to the subject B at a preset angle of X-ray source 10 (for example, −20 degrees, −10 degrees, 0 degree, 10 degrees, and 20 degrees when the number of X-ray irradiation times is 5) depending on the number of X-ray irradiation times which is preset in the operation control unit 70 during continuous rotation.

Figure 8:
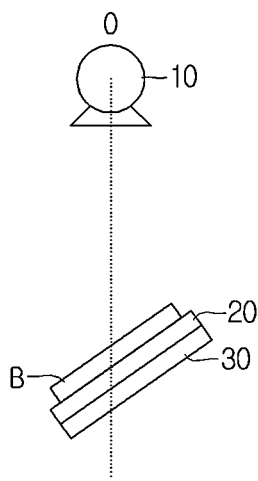

Further, prior to the intermittent rotation of the X-ray source 10, the subject support 20 may be rotated in accordance with the preset angle range (for example, −90 degrees to 90 degrees) as illustrated in FIG. 8, and since the 2D images with respect to an interest region in the subject B may not be easily acquired in accordance with the thickness of the subject B when the subject support 20 is in a horizontal state, the subject support 20 may be rotated in accordance with the preset angle range prior to the intermittent rotation of the X-ray source 10 as such to prevent the problem and accurately acquire the 2D images with respect to the interest region in the subject B.

Figure 9:
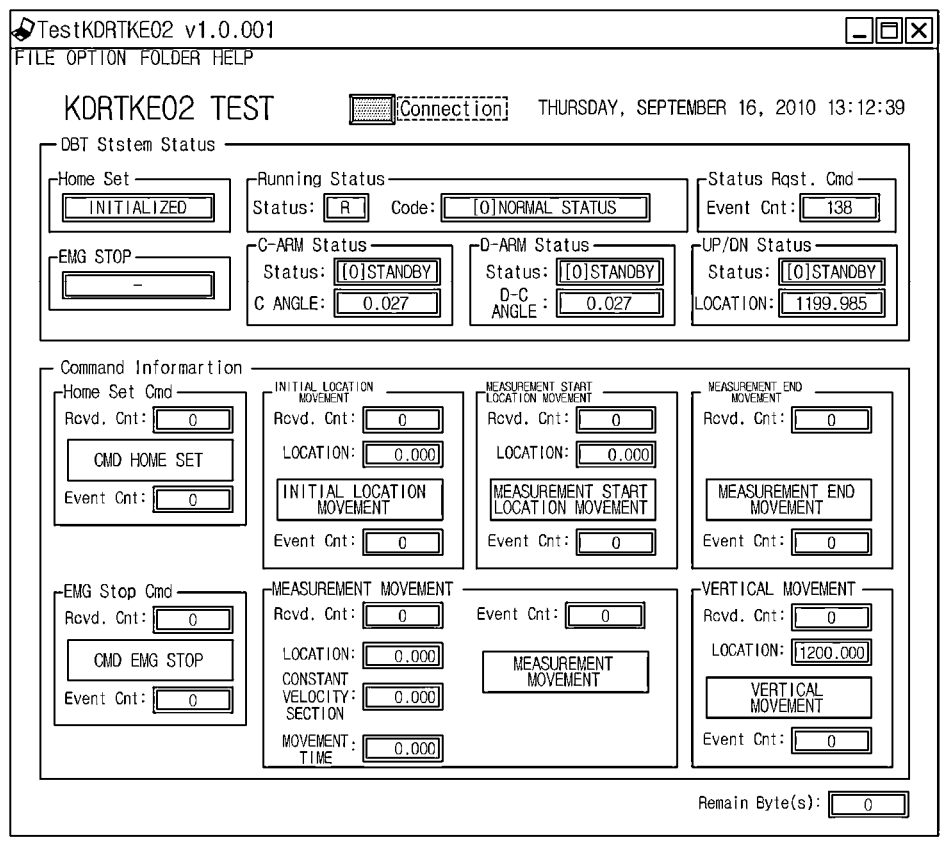
FIGS. 9 and 10 are reference diagrams of a screen of an operation control unit of FIG. 2.
Figure 10:
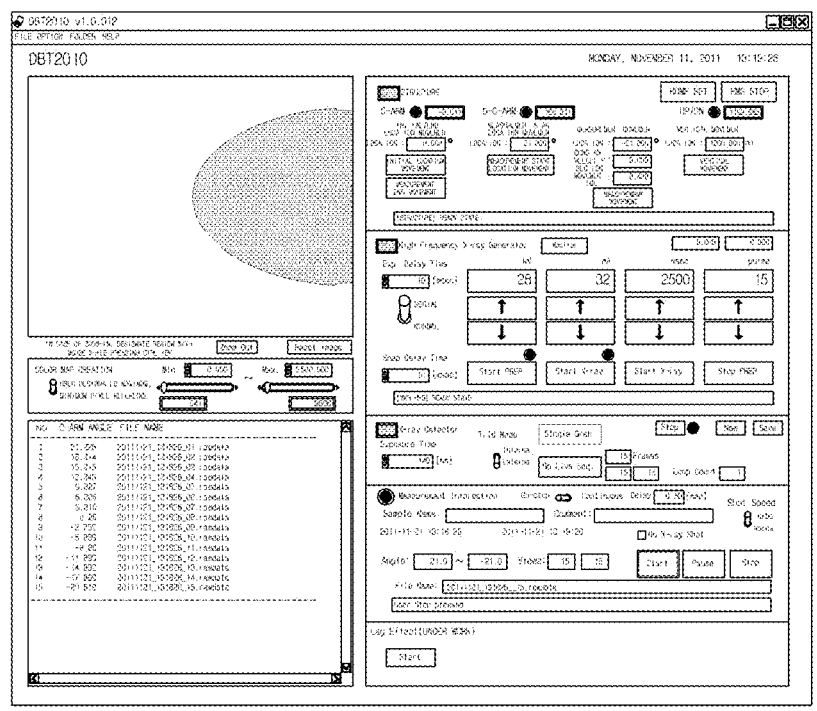

FIGS. 9 and 10 are reference diagrams for a display screen of an operation control unit.

As illustrated in FIG. 9, the operation control unit controls the angles of the X-ray source 10 and the subject support 20 by automatically controlling the operations of the first driving unit 50 and the second driving unit 60 by user's input using an additional display means and an additional input means to control the focus of the X-ray irradiated from the X-ray source 10 to the subject B.

As illustrated in FIG. 10, the operation control unit 70 may automatically control the intensity of the X-ray irradiated from the X-ray source 10 by the user's input using the additional display means and input means.

Further, the operation control unit 70 controls the X-ray source 10 to be automatically rotated within an angle range set by user's angle range setting using the additional display means and input means as illustrated in FIG. 9, and may control the X-ray source 10 to generate the X-ray when stopping at a preset angle during intermittent rotation or control the X-ray source 10 to generate the X-ray at a preset angle during continuous rotation automatically at the preset number of irradiation times by user's setting the number of X-ray irradiation times.

For example, when a user sets the angle range to −15 degrees to 15 degrees and sets the number of irradiation times to 10, the operation control unit 70 may control the X-ray source 10 to rotate at approximately 4.3□/s and genetate the X-ray ten times by considering a case in which the X-ray source 10 stops in order to genetate the X-ray.

Further, the operation control unit 70 may control the X-ray source 10 similarly in accordance with a different set angle and the different number of irradiation times.

Further, the operation control unit 70 may control a corresponding image to be automatically displayed on the display means so that the user verifies the 3D image in person as illustrated in FIG. 9.

Figure 11:
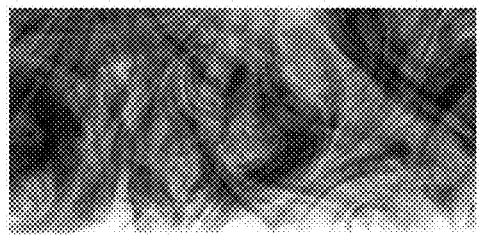
FIG. 11 is a reference diagram for 2D images and a 3D image according to an exemplary embodiment of the present invention.
Figure 11:
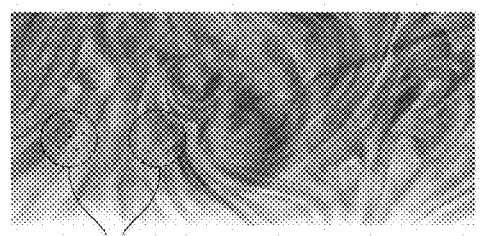

FIG. 11 is a reference diagram for the 2D images and the 3D image according to the exemplary embodiment of the present invention.

In the 2D images with respect to the subject illustrated in FIG. 11(*a*), the presence or absence of the lesion in the subject B is not easily determined, while in the case of the 3D image with respect to the diagnosis subject illustrated in FIG. 11(*b*), the presence or absence of the lesion C with respect to the subject B may be definitely determined, so that the lesion of the person to be diagnosed may be precisely diagnosed.

Figure 12:
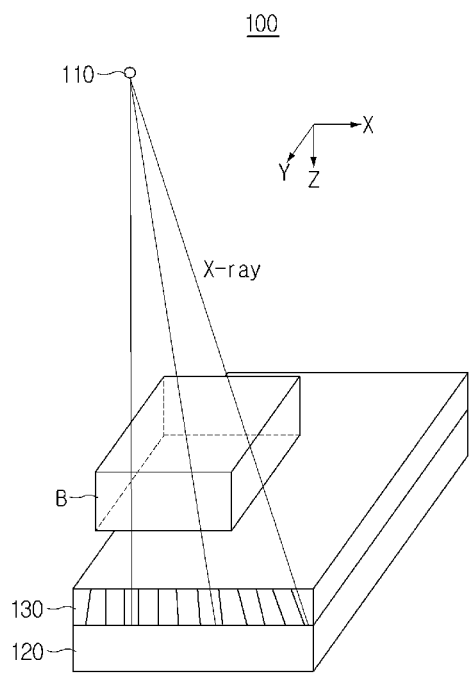
FIG. 12 is a perspective view of an apparatus for diagnosing lesions according to another exemplary embodiment of the present invention.
Figure 13:
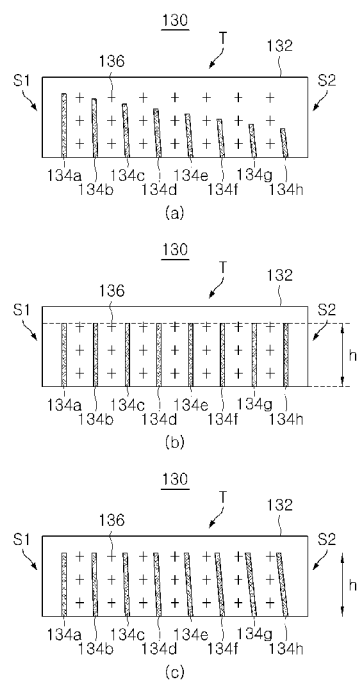
FIG. 13 is a cross-sectional view of a grid of FIG. 12.

FIG. 12 is a perspective view of an apparatus for diagnosing lesions according to another exemplary embodiment of the present invention. FIG. 13 is a cross-sectional view of a grid of FIG. 12.

As illustrated in FIGS. 12 and 13, the apparatus 100 for diagnosing lesions according to another exemplary embodiment of the present invention includes a grid 130 positioned between the subject B and the subject support 120, and since the rest of the components other than the grid 130 are the same as those of the apparatus 1 for diagnosing lesions according to the exemplary embodiment of the present invention, the rest of the components are not additionally illustrated and a detailed description thereof will also be omitted.

The grid 130 includes a body part 132 which the X-ray generated from the X-ray source 110 transmits after passing through the subject B, a plurality of partitions 134*a* 134*b* 134*c* 134*d* 134*e* 134*f* 134*g* 134*h* provided in the body part 132 at a predetermined interval, and a transmission member 136 filled in an inner space of the body part 132 other than the plurality of partitions 134*a* 134*b* 134*c* 134*d* 134*e* 134*f* 134*g* 134*h*.

In this case, the body part 132 may be made of plastic, polymer, ceramic, graphite, or a carbon fiber which is excellent in X-ray transmittivity, and the plurality of partitions 134*a* 134*b* 134*c* 134*d* 134*e* 134*f* 134*g* 134*h* may be made of lead capable of shielding the body part 134 from the X-ray that transmits the body part 134, and the transmission member 136 may be made of carbon or acryl which has excellent X-ray transmittivity.

Further, although not illustrated in the figure, a plurality of grooves is formed to have a predetermined interval in a height direction in the body part 132 instead of filling the transmission member 136 in the inner space of the body part 132 and thereafter, lead is filled in the formed grooves, and as a result, the plurality of partitions may 134a 134b 134c 134d 134e 134f 134g 134h also be configured in the body part 132.

Further, as illustrated in FIG. 13, the plurality of partitions 134a 134b 134c 134d 134e 134f 134g 134h positioned in the body part 132 is arranged in such manner that an interval between the plurality of partitions 134a 134b 134c 134d 134e 134f 134g 134h and the top surface T of the body part 132 is widened from one side S1 to the other side S2 in the body part 132, the rest of partitions other than the partition 134a positioned at one side S1 among the plurality of partitions 134a 134b 134c 134d 134e 134f 134g 134h are arranged to be inclined at a predetermined angle with respect to the vertical direction (FIG. 13(a), the plurality of partitions 134a 134b 134c 134d 134e 134f 134g 134h having the same height h is arranged in the vertical direction (FIG. 13(b)), or the rest of the partitions other than the partitions 134a 134b 134c 134d 134e 134f 134g 134h having the same height h may be arranged to be inclined at the predetermined angle with respect to the vertical direction (FIG. 13(c)).

In this case, the rest of the partitions are preferably arranged in such a manner that an angle at which the rest of the partitions other than the partitions 134a positioned at one side S1 in the body part 132 in FIGS. 13(a) and 13(c) are inclined to the vertical direction gradually increases from the one side S1 to the other side S2 in the body part 132.

Further, the reason for arranging the partitions 134a positioned at one side S1 in the body part 132 in the vertical direction in FIGS. 13(a) and 13(c) is that the X-ray source 110 is positioned vertically above the partitions 134a positioned at one side S1 even though the X-ray source 110 intermittently or continuously rotates, and the reason for configuring the grid 130 as illustrated in FIGS. 13(a), 13(b), and 13(c) is described as below.

An X-ray irradiated in 2D mammography in the related art is irradiated unidirectionally (that is, vertically to the subject), while in the case of the apparatus 100 for diagnosing lesions according to another exemplary embodiment of the present invention, the X-ray source 110 intermittently or continuously rotates in order to acquire the 3D image with respect to the subject and the generated X-ray is irradiated to the subject B at a preset angle when the X-ray source 110 stops at a preset angle during the intermittent rotation or during the continuous rotation.

Therefore, the height of the X-ray source 110 is changed with the intermittent or continuous rotation of the X-ray source 110, and as a result, an angle between an X-ray source 110 and the bottom surface of the grid 130 is continuously changed. Therefore, when a grid used in the related art is just applied, the X-ray irradiated from the X-ray source 110 may be cut off in the grid, and since a primary X-ray that transmits the subject B and thereafter, is projected to the X-ray detector is reduced in accordance with such a cut-off phenomenon, an image contrast of the 2D images may be degraded and image noise such as aliasing and moire may be generated from the 2D images. Accordingly, the generated X-ray is irradiated to the subject B in such a manner in order to prevent the problems.

Figure 14:
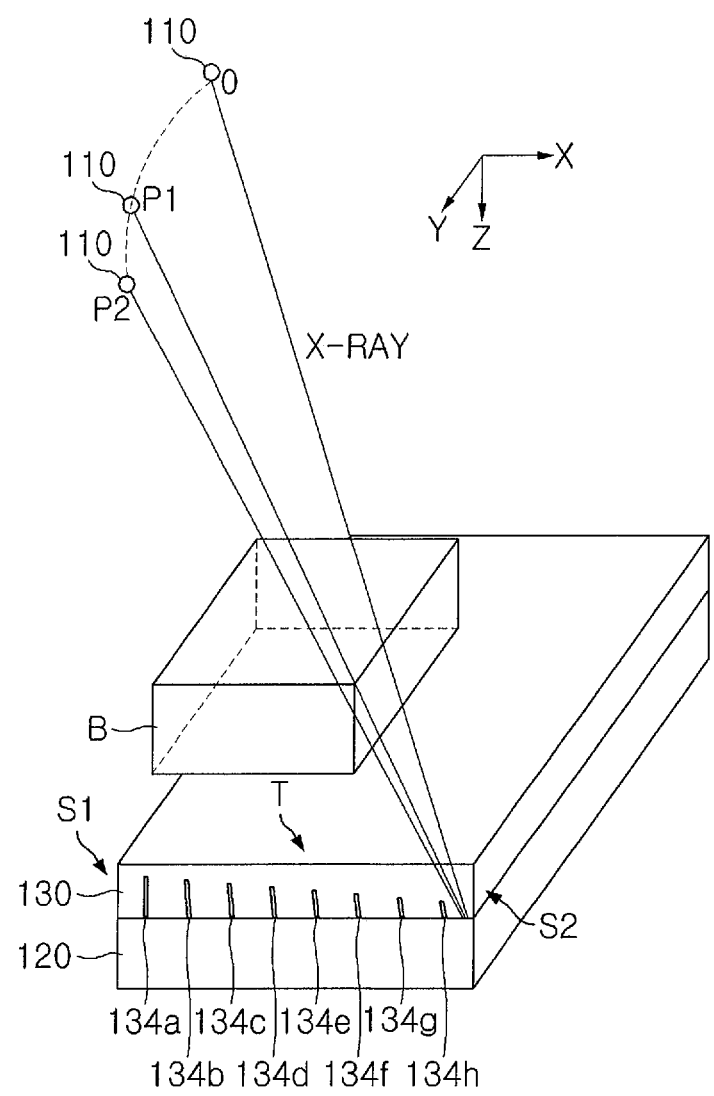
FIGS. 14 to 16 are operation reference diagrams of the apparatus for diagnosing lesions according to another exemplary embodiment of the present invention.
Figure 15:
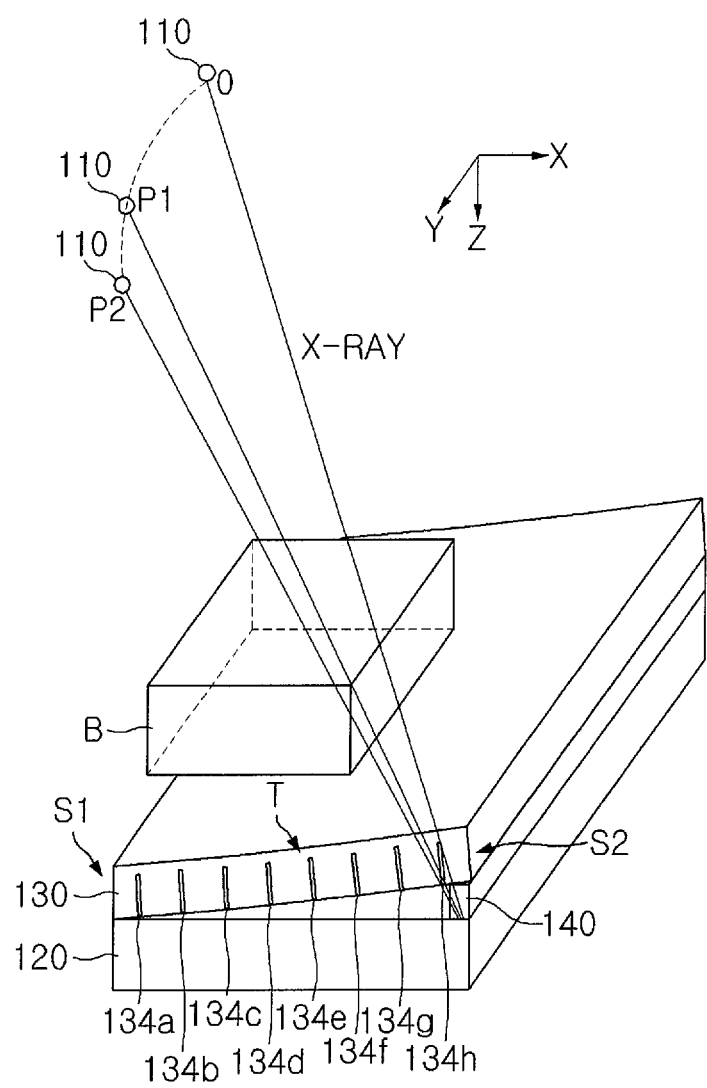
Figure 16:
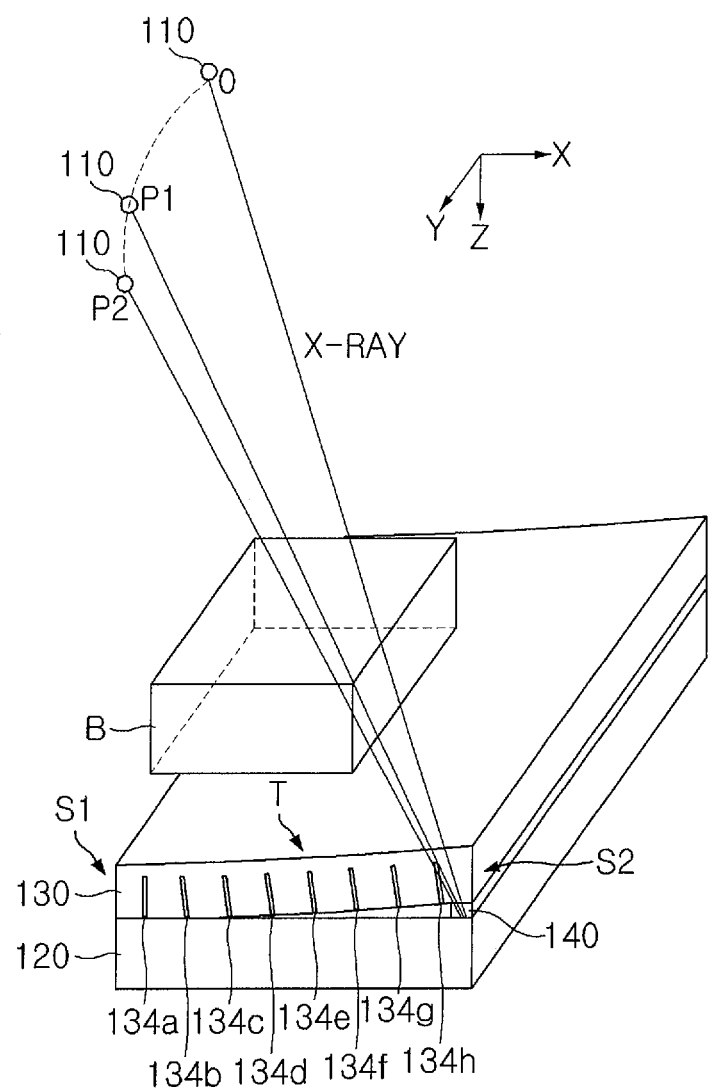

FIGS. 14 to 16 are operation reference diagrams of the apparatus for diagnosing lesions according to another exemplary embodiment of the present invention.

FIG. 14 is an operation reference diagram when the grid 130 illustrated in FIG. 13(a), that is, the grid 130 in which the plurality of partitions 134a 134b 134c 134d 134e 134f 134g 134h arranged in the body part 132 is arranged in such a manner that a height between the partitions 134a 134b 134c 134d 134e 134f 134g 134h and the top surface T of the body part 132 is reduced from one side S1 to the other side S2 of the body part 132 and the rest of the partitions other than the partition 134a positioned at one side S1 among the plurality of partitions 134a 134b 134c 134d 134e 134f 134g 134h are arranged to be inclined at a predetermined angle with respect to the vertical direction is positioned between the subject B and the subject support 120.

As illustrated in FIG. 14, when the X-ray source 110 rotates from the initial location O to predetermined points P1 and P2 unidirectionally as illustrated in FIG. 14, the height of the X-ray source 110 is decreased.

However, since the plurality of partitions 134a 134b 134c 134d 134e 134f 134g 134h arranged in the body part 132 of the grid 130 is arranged in such a manner that the height between the partitions 134a 134b 134c 134d 134e 134f 134g 134h and the top surface T of the body part 132 is decreased from one side S1 to the other side S2 of the body part 132 and the rest of the partitions other than the partition 134a positioned at one side S1 among the plurality of partitions 134a 134b 134c 134d 134e 134f 134g 134h are arranged to be inclined at a predetermined angle with respect to the vertical direction, it is possible to prevent the X-ray passing through the subject B from being cut-off due to collision with the plurality of partitions 134a 134b 134c 134d 134e 134f 134g 134h while transmitting the grid 130 even though the height of the X-ray source 110 is decreased.

FIG. 15 is an operation reference diagram when the grid 130 illustrated in FIG. 13(b), that is, the grid 130 in which the plurality of partitions 134a 134b 134c 134d 134e 134f 134g 134h arranged in the same height h in the body part 132 is arranged in the body part 132 in the vertical direction is positioned between the subject B and the subject support 120.

In this case, as illustrated in FIG. 15, the apparatus 100 for diagnosing lesions may further include a height adjustment unit 140 that is coupled between the other side S2 of the bottom surface of the body part 132 and the top surface of the subject support 120, and adjusts the height of the other side S2 of the body part 132 by a predetermined height in accordance with the intermittent or continuous rotation of the X-ray source 110.

Further, since the height adjustment unit 140 adjusts the height of the other side S2 of the body part 132 depending on the position of the X-ray source 110 when the X-ray source 110 rotates to reach the predetermined points P1 and P2 from the initial location O, the other side S2 of the bottom surface of the body part 132 may have an inclination angle having a predetermined value by an operation of the height adjustment unit 140 even when the plurality of partitions 134a 134b 134c 134d 134e 134f 134g 134h arranged in the body part 132 of the grid 130 is vertically arranged in the same height as illustrated in FIG. 13(b).

Accordingly, even though the height of the X-ray source 110 is decreased, it is possible to prevent the X-ray passing through the subject B from being cut-off by colliding with the plurality of partitions 134a 134b 134c 134d 134e 134f 134g 134h while transmitting the grid 130.

Further, the height adjustment unit 140 may be a memory alloy, an electromagnet, or a separate machine device which may move up or down.

Herein, the predetermined inclination angle may be in the range of 19 degrees to 22 degrees, and more preferably, 19.2 degrees to 21.9 degrees.

As one example, when the initial height (the location O of FIG. 14) of the X-ray source 110 is 660 mm, the height (the point P1 of FIG. 14) of the X-ray source 110 when the X-ray source 110 rotates unidirectionally at 20 degrees is 620 mm, and the height (the point P2 of FIG. 14) of the X-ray source 110 when the X-ray source 110 rotates unidirectionally at 30 degrees is 572 mm, and the width of the grid 130 is 230 mm, the inclination angles of the X-ray that is irradiated from the X-ray source 110 to transmit the other side S2 of the bottom surface of the body part 132 may be 70.8 degrees, 69.6 degrees, and 68.1 degrees, respectively.

Accordingly, the inclination angles of the other side S2 of the bottom surface of the body part 130 formed by the operation of the height adjustment unit 140 is set to 19.2 degrees, 20.4 degrees, and 21.9 degrees by considering the inclination angles of the X-ray to prevent the X-ray passing through the subject B from being cut off by colliding with the plurality of partitions 134a 134b 134c 134d 134e 134f 134g 134h while transmitting the grid 130.

FIG. 16 is an operation reference diagram when the grid 130 illustrated in FIG. 13(c), that is, the grid 130 in which the rest of the partitions other than the partition 134a positioned at one side S1 in the body part 132 among the plurality of partitions 134a 134b 134c 134d 134e 134f 134g 134h arranged in the same height h in the body part 132 are arranged to be inclined at a predetermined angle to the vertical direction is positioned between the subject B and the subject support 120.

As illustrated in FIG. 16, the apparatus 100 for diagnosing lesions may further include a height adjustment unit 140 that is coupled between the other side S2 of the bottom surface of the body part 132 and the top surface of the subject support 120, and adjusts the height of the other side of the body part 132 by a predetermined height in accordance with the intermittent or continuous rotation of the X-ray source 110.

In this case, since the height adjustment unit 140 adjusts the height of the other side S2 of the body part 132 depending on the position of the X-ray source 110 when the X-ray source 110 rotates to reach the predetermined points P1 and P2 from the initial location O, the other side S2 of the bottom surface of the body part 132 may have an inclination angle having a predetermined value by the operation of the height adjustment unit 140 even when the rest of partitions other than the partition 134a positioned at one side S1 in the body part 132 among the plurality of partitions 134a 134b 134c 134d 134e 134f 134g 134h arranged in the body part 132 of the grid 130 in the same height h are arranged to be inclined at a predetermined angle with respect to the vertical direction as illustrated in FIG. 13(c).

Accordingly, even though the height of the X-ray source 110 is decreased, it is possible to prevent the X-ray passing through the subject B partitions 134a 134b 134c 134d 134e 134f 134g 134h while transmitting the grid 130.

Herein, the predetermined inclination angle may be at the maximum range of 2 degrees to 4 degrees, and more preferably, 2.7 degrees. As compared with the grid 130 illustrated in FIG. 13(b), the rest of partitions other than the partition 134a positioned at one side S1 in the body part 132 among the plurality of partitions 134a 134b 134c 134d 134e 134f 134g 134h are arranged to be inclined at the predetermined angle with respect to the vertical direction, and therefore, it is possible to lower the inclination angle of the other side S2 of the bottom surface of the body part 130 formed by the operation of the height adjustment unit 140.

Figure 17:
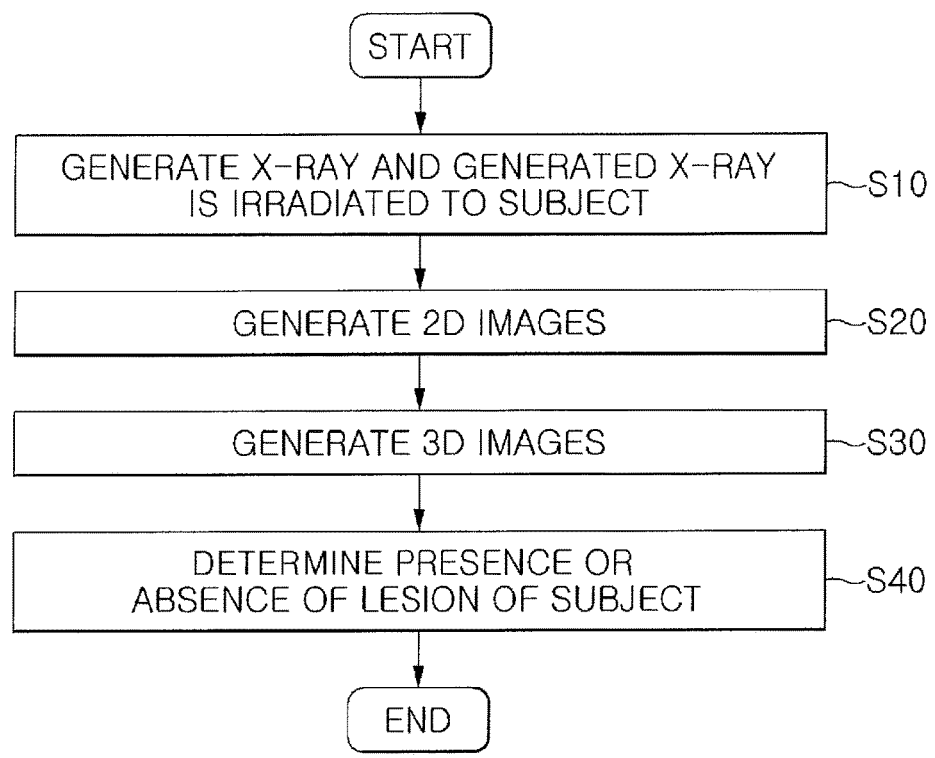
FIG. 17 is a flowchart of a method for diagnosing lesions according to an exemplary embodiment of the present invention.

FIG. 17 is a flowchart of a method for diagnosing lesions according to an exemplary embodiment of the present invention.

As illustrated in FIG. 17, X-ray source 10 and 110 generate X-rays and the generated X-rays is irradiated to a subject in S10.

In this case, in S10, the X-ray source 10 and 110 may be an X-ray tube and rotate intermittently or continuously in accordance with a preset angle range and may generate the X-rays only when stops at a preset angle during intermittent rotation, or genetate the X-rays at a preset angle during continuous rotation.

Further, a detailed process of S10 will be described below with reference to FIG. 28.

Further, subsequent to S10, the method may further include a step in which the X-ray irradiated from the X-ray source 110 passes through the subject B and thereafter transmits a grid 130 positioned between the subject B and a subject support 110, and since a detailed configuration of the grid 130 has been described as above, the detailed configuration will not be described.

In S20, the X-ray detector 30 and 120 generate 2D images with respect to the subject from the X-rays passing through the subject.

In this case, the X-ray detector 30 and 120 may be a digital type semiconductor flat panel detector, and the 2D images may be a plurality of projected images with respect to a subject B generated in a plurality of locations by the X-rays passing through the subject B in accordance with rotation of the X-ray source 10 and 110.

In S30, a lesion determination unit 40 generates a 3D image with respect to the subject B by using the 2D images generated by the X-ray detector 30 and 120.

In this case, since the 3D image is generated by combining 2D images passing through the subject B at various angles by rotation of the X-ray source 10 when the presence or absence of a lesion at a specific location of the subject B is determined, it is possible to more precisely determine a state of the lesion with respect to the specific location.

For example, when the X-ray is irradiated only unidirectionally in the case where a plurality of lesions is present in a vertical direction, it is not easy to precisely determine a lesion state by overlapping of the plurality of lesions, but in the case of the 3D image acquired by combining the 2D images passing through the subject B at various angles, it is possible to precisely determine the lesion state even in the case of the plurality of lesions that exists in the vertical direction.

In S40, when the lesion determination unit 40 determines the presence or absence of the lesion (for example, breast cancer) of the subject from the 3D image, the process ends.

Further, prior to S10, the method may further include a step of calibrating a focus location of the X-ray irradiated from the X-ray source 10, and the step of calibrating the focus location of the X-ray may be divided into a method of calibrating the focus location of the X-ray by using the X-ray projected image which is the 2D image and a method of calibrating the position of the X-ray source 10, and the former will be described below in detail with reference to FIGS. 18 to 22 and the latter will be described in detail with reference to FIGS. 23 to 27.

Figure 18:
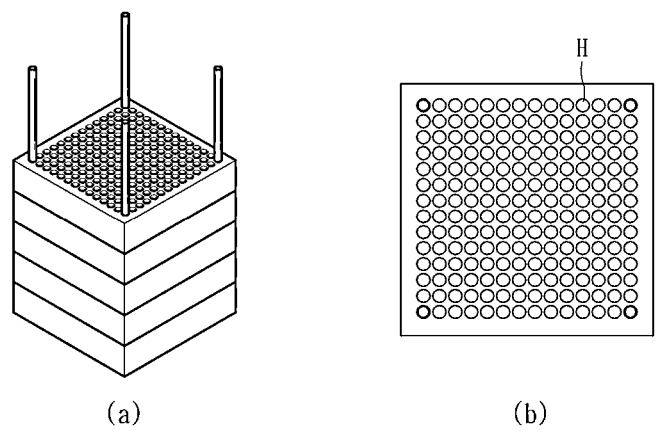
FIG. 18 is a reference diagram of a calibration phantom.
Figure 19:
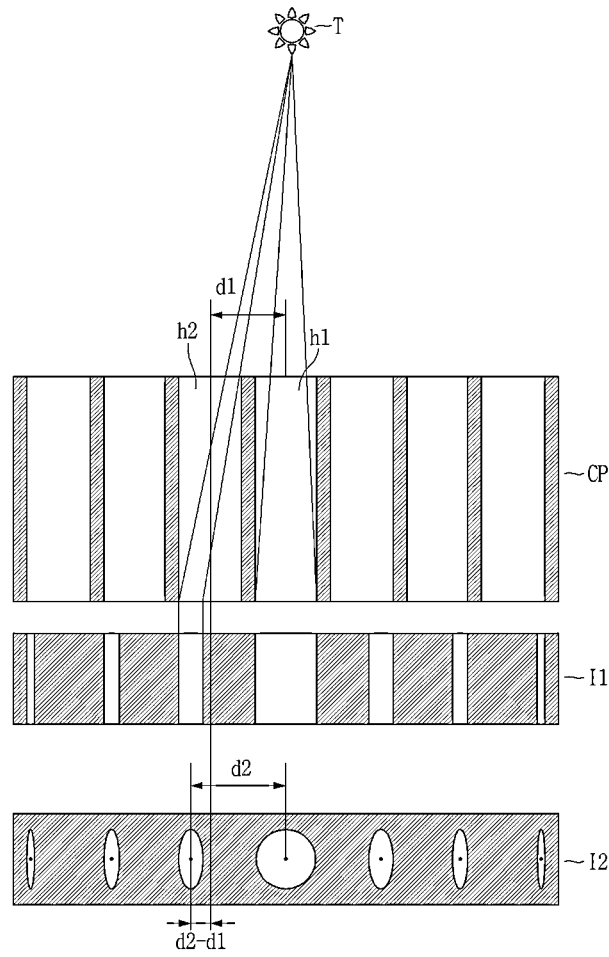
FIG. 19 is a reference diagram of a plane image for an X-ray passing through the calibration phantom.

FIG. 18 is a reference diagram of a calibration phantom.
FIG. 19 is a reference diagram of a plane image for an X-ray passing through the calibration phantom.

As illustrated in FIG. 18, the calibration phantom used to calibrate the X-ray focus location is configured by a pattern in which five multi-hole collimators each having 196 holes are stacked (FIG. 18(a)) and the diameter of the hole H formed in each multi-hole collimator may be 1.5 mm, an interval of the respective holes may be 2 mm, and the depth of the hole may be 50 mm (FIG. 18(b)).

As illustrated in FIG. 19, as compared with an X-ray vertically passes through a hole h1 formed at the center of calibration phantom CP, an X-ray passes through a hole h2, by a predetermined distance, spaced from the hole h1 passes through the hole h2 at a predetermined angle, and as a result, the width of the X-ray passes through the hole h2 is narrow than the width of the X-ray passes through a hole h1 by a partition between the holes h1 and h2.

Therefore, when a plane image I2 for the X-ray passing through the calibration phantom CP is verified, the hole h1 formed at the center of the calibration phantom CP is displayed in a circle shape on the plane image I2 by the X-ray passing through the hole h1 formed at the center of the calibration phantom CP, while the hole h2, by predetermined distance, spaced from the hole h1 formed at the center of the calibration phantom CP has an oval shape similar to a rugby ball shape on the plane image I2 by the narrow width of the X-ray and as the hole is farther spaced from the hole h1 formed at the center of the calibration phantom CP, the hole displayed on the plane image I2 may be narrowed.

Further, an actual distance d1 between both holes h1 and h2 formed in the calibration phantom CP and a distance d2 between both holes h1 and h2 formed in the calibration phantom CP which may be verified on the plane image I2 are different from each other by the narrow width of the X-ray.

Figure 20:
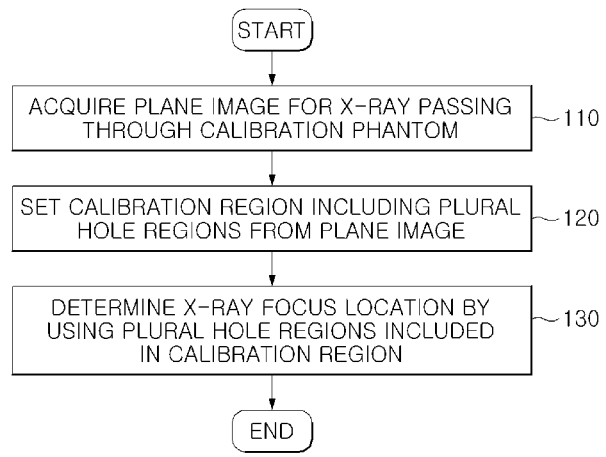
FIG. 20 is a flowchart of a method for calibrating an X-ray focus location according to an exemplary embodiment of the present invention.
Figure 21:
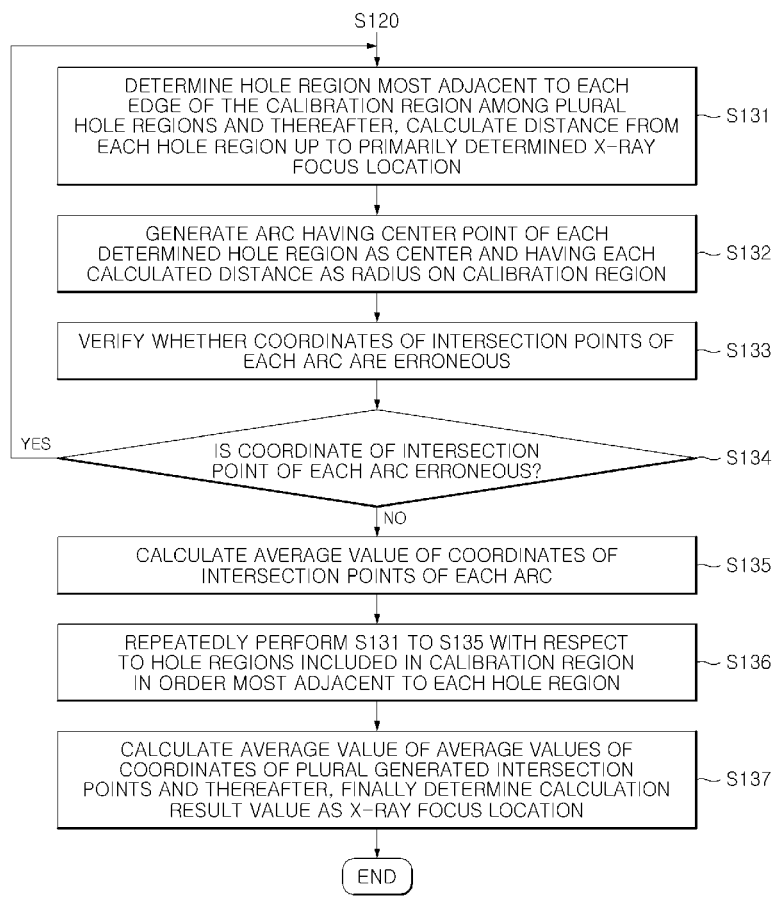
FIG. 21 is a detailed flowchart for S130 of FIG. 20.
Figure 22:
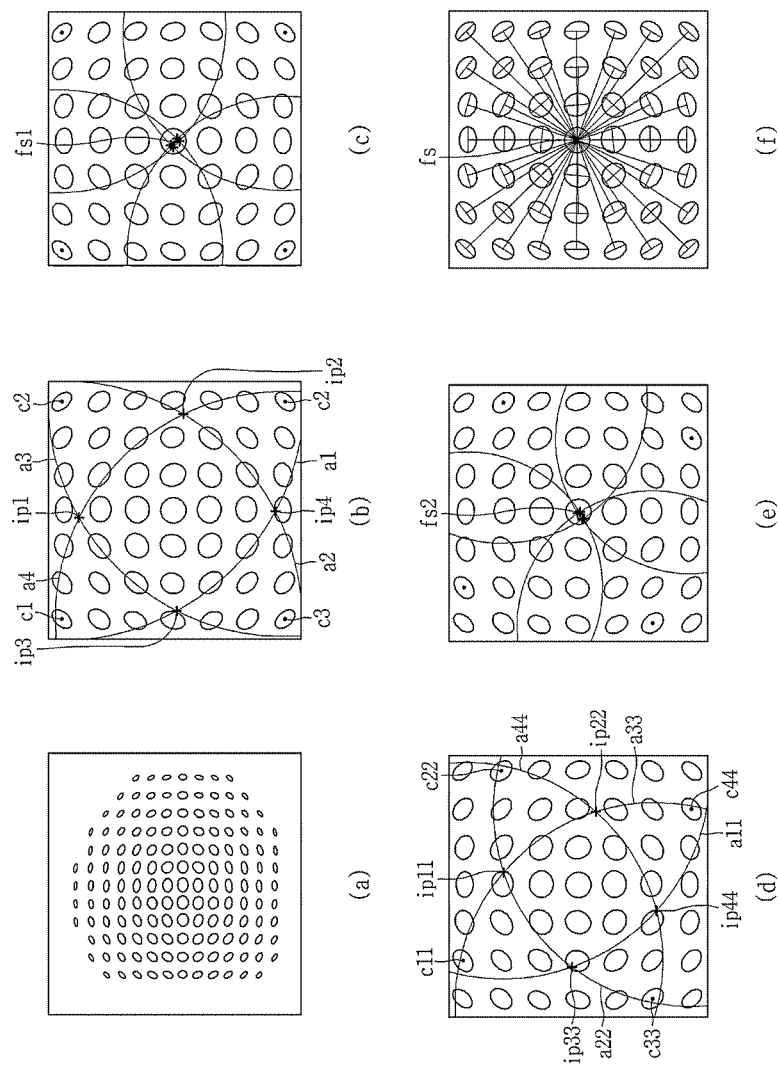
FIG. 22 is a reference diagram of the method for calibrating an X-ray focus location according to an exemplary embodiment of the present invention.

FIG. 20 is a flowchart of a method for calibrating an X-ray focus location according to an exemplary embodiment of the present invention. FIG. 21 is a detailed flowchart for S130 of FIG. 20. FIG. 22 is a reference diagram of the method for calibrating an X-ray focus location using a calibration phantom according to an exemplary embodiment of the present invention.

In S110, the plane image for the X-ray passing through the calibration phantom CP is acquired.

In this case, the plane image for the X-ray passing through the calibration phantom CP may include a plurality of hole regions that is formed by the plurality of holes formed in the calibration phantom CP as illustrated in FIG. 22(a).

In S120, a calibration region including the plurality of hole regions formed by the plurality of holes is set from the plane image acquired in S110.

In this case, the calibration region may be set to have a quadrate shape or a rectangular shape as illustrated in FIG. 22(b), and the number of the plurality of hole regions included in the calibration region may be 49 (7×7) or 64 (8×8) as illustrated in FIG. 22(b) when the calibration region has the quadrate shape and 42 (6×7) or 63 (7×9) when the calibration region has the rectangular shape.

Further, the size of a single pixel constituting the calibration region may be 0.075 mm×0.075 mm and the size of an X-ray focus on the calibration region may be 0.3 mm×0.3 mm.

In S130, when the X-ray focus location is decided by using the plurality of hole regions included in the calibration region set in S120, the process ends.

In this case, a detailed process of S130 will be described below in detail with reference to FIGS. 21 and 22.

Hole regions (c1, c2, c3, and c4 in FIG. 22(b)) most adjacent to each edge of the calibration region among the plurality of hole regions included in the set calibration region are determined in S131 as illustrated in FIG. 21 and thereafter, distances up to the X-ray focus location primarily determined on the calibration region from center points of the determined respective hole regions (c1, c2, c3, and c4 in FIG. 22(b)) are calculated.

In this case, as the X-ray focus location primarily determined on the calibration region, the center of a hole region in which a ratio value of the hole region of the calibration phantom CP to the area is closest to 1 may be decided, in other words, the X-ray focus location may be the center of a hole region having the most similar shape to the circular shape which is the shape of the hole predetermined by the calibration phantom CP among the plurality of hole regions included in the calibration region.

Further, the distance up to the X-ray focus location primarily determined on the calibration region from each determined hole region in S131 may be calculated by an equation below.

$$r_i = d \times \left(1 - \frac{A_i}{A_c}\right) \qquad \text{[Equation 1]}$$

Herein, ri represents a distance up to the primarily determined X-ray focus location from a hole region i, d represents a distance up to the center of the hole region most adjacent to the edge of the calibration region froth the X-ray focus location primarily determined on the calibration region, Ai represents an area of the hole region i, and Ac represents an area of the hole formed in the calibration phantom.

In S132, an arc (a1, a2, a3, or a4 in FIG. 22(b)) having the center point of each hole region determined on the calibration region as the center and each calculated distance as a radius is generated.

In S133, it is verified whether x and y coordinate values of an intersection point (ip1, ip2, ip3, or ip4 in FIG. 22(b)) generated by each generated arc (a1, a2, a3, or a4 in FIG. 22(b)) are erroneous.

In this case, it may be verified whether the x and y coordinate values of the intersection point (ip1, ip2, ip3, or ip4 in FIG. 22(b)) are erroneous by verifying whether a distribution value of the x coordinate values and a distribution value of the y coordinate values of the intersection point (ip1, ip2, ip3, or ip4 in FIG. 22(b)) are more than predetermined reference values and the predetermined reference values may be the lengths of three pixels among a plurality, of pixels constituting the calibration region (for example, 0.075×3=0.225 mm).

In S134, when the distribution values of the x and y coordinate values of the intersection points are more than the predetermined reference value, it is determined that the x and y coordinate values of intersection points are erroneous, and as a result, steps S131 to S133 are repeatedly performed and when the distribution values of the x and y coordinate values of the intersection points are equal to or less than the predetermined reference value, it is determined that the x and y coordinate values of intersection points are not erroneous, and as a result, average values of the x and y coordinate values of the intersection points are calculated in S135 (fs1 in FIG. 22(c)).

In this case, when the distribution values of the x and y coordinate values of the intersection points are more than the predetermined reference values, the distance up to the primarily determined X-ray focus location on the calibration region from each determined hole region is recalculated by adjusting a value of d of Equation 1 above, and as a result, the redetermined distribution values of the x and y coordinate values of the intersection points may not be more than the predetermined reference values (FIG. 22(c)).

In S136, the hole regions are selected in an order most adjacent to the respective hole regions (c1, c2, c3, and c4 in FIG. 22(b)) determined in S131 (c11, c22, c33, and c44 in FIG. 22(d)), distances up to the primarily determined X-ray focus location on the calibration region from the center points of the respective selected hole regions are calculated and thereafter, arcs (a11, a22, a33, and a44 in FIG. 22(d)) having center points of the respective selected hole regions as the center and the respective calculated distances as the radius are generated, and it is verified whether x and y coordinate values of intersection points (ip11, ip22, ip33, and ip44 in FIG. 22(d)) generated by the respective generated arcs (a11, a22, a33, and a44 in FIG. 22(d)) are erroneous and thereafter, when the x and y coordinate values are not erroneous, steps S131 to S135 are repeatedly performed with respect to all of the hole regions included in the calibration region by calculating average values (fs2 in FIG. 22(e)) of the x and y coordinate values of the intersection points (ip11, ip22, ip33, and ip44 in FIG. 22(d)).

In S137, an average value of the average values of the coordinates of the plurality of intersection points generated in S131 to S136 is calculated and thereafter, when the calculation result value is finally determined as the X-ray focus location (fs in FIG. 22(f)), calibration of the X-ray focus location may be completed.

FIGS. 23 to 27 are reference diagrams of an X-ray focus calibration method according to another exemplary embodiment of the present invention.

Figure 23:
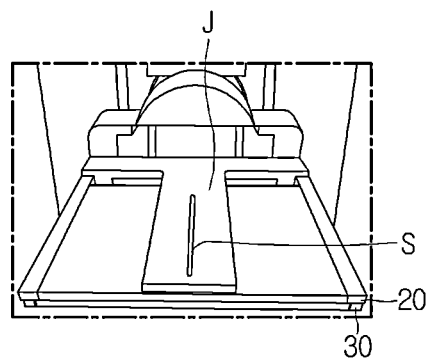
FIGS. 23 to 27 are reference diagrams of a focus calibration method of an X-ray source.
Figure 24:
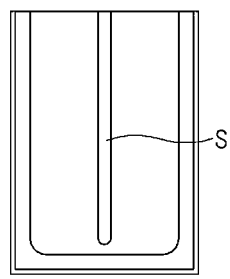

When a slit jig J having a slit S at the center thereof is coupled to the upper portion of the subject support 20 and thereafter, the X-ray is irradiated from the X-ray source 10 to the slit jig J as illustrated in FIG. 23, a projected image for the slit jig J in which the slit S is displayed with a white color in the X-ray detector 30 and the remaining portions are displayed with a black color is generated as illustrated in FIG. 24.

In addition, it may be verified whether a focus of the X-ray irradiated from the X-ray source 10 to the subject support 20 matches the center of the subject support 20 by using the projected image for the slit jig J, and as one example, when a pixel number of a sensor corresponding to the center of the subject support 20 among sensors of a matrix pattern, which constitute the X-ray detector 30 and a pixel number of a location where the projected image for the slit S is generated coincide with each other, it may be determined that the focus of the X-ray matches the center of the subject support 20, and when the pixel numbers does not coincide with each other, the focus of the X-ray may match the center of the subject support 20 by adjusting an angle of the X-ray source 10 by the operation control unit 70.

Figure 25:
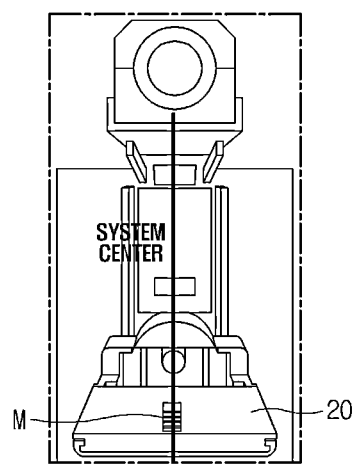
Figure 26:
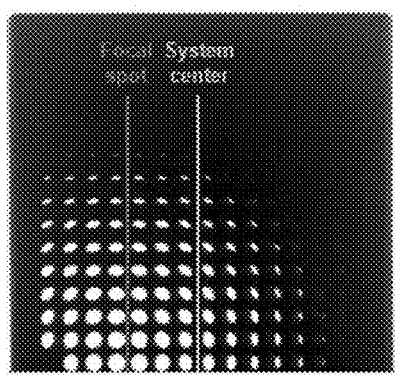
Figure 26:
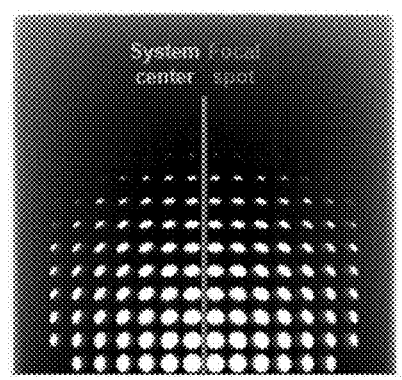

Further, when a measurement assisting device M having a plurality of pin holes is positioned above the subject support 20 in such a manner that a center axis of the measurement assisting device M matches the center axis of the X-ray source 10 as illustrated in FIG. 25 and the X-ray is irradiated from the X-ray source 10 to the measurement assisting device M, a projected image of the measurement assisting device M in which pin hole portions are displayed with the white color and the remaining portions are displayed with the black color may be generated by the 30 as illustrated in FIGS. 26(a) and 26(b).

In this case, when the center axis (system center) of the X-ray source 10, which is set at the time of initially designing the apparatus 1 for diagnosing lesions does not match the center axis (focal center) of the X-ray source 10 which may be verified from the projected image of the actual measurement assisting device M as illustrated in FIG. 26(a), the focus of the X-ray irradiated from the X-ray source 10 may match the center of the subject support 20 by adjusting the angle of the X-ray source 10 so that both center axes match each other as illustrated in FIG. 26(b).

Figure 27:
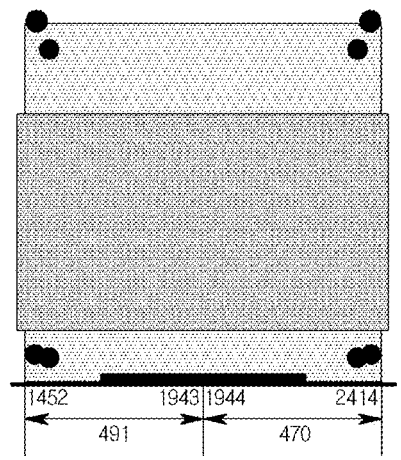
Figure 27:
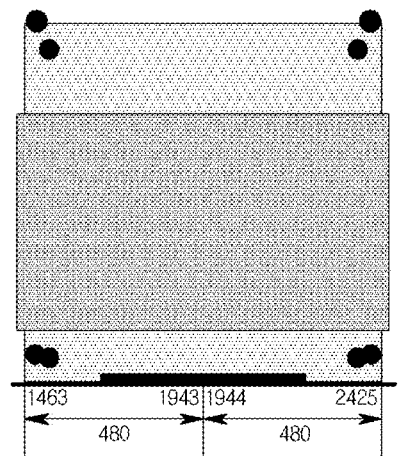

Further, a phantom having a stereoscopic rectangular shape, which the X-ray transmits, which is illustrated in FIG. 27 and including a plurality of bearings provided in the upper portion and the lower portions thereof, which are symmetric to each other is positioned above the subject support 20 in such a manner that a center axis thereof matches the center axis of the X-ray source 10 and thereafter, a projected image for the phantom, which is generated by the X-ray is verified, and when the projected image for the phantom is not laterally symmetric as illustrated in FIG. 27(a), the focus of the X-ray may match the center of the subject support 20 as illustrated in FIG. 27(b) by adjusting the angle of the X-ray source 10.

Figure 28:
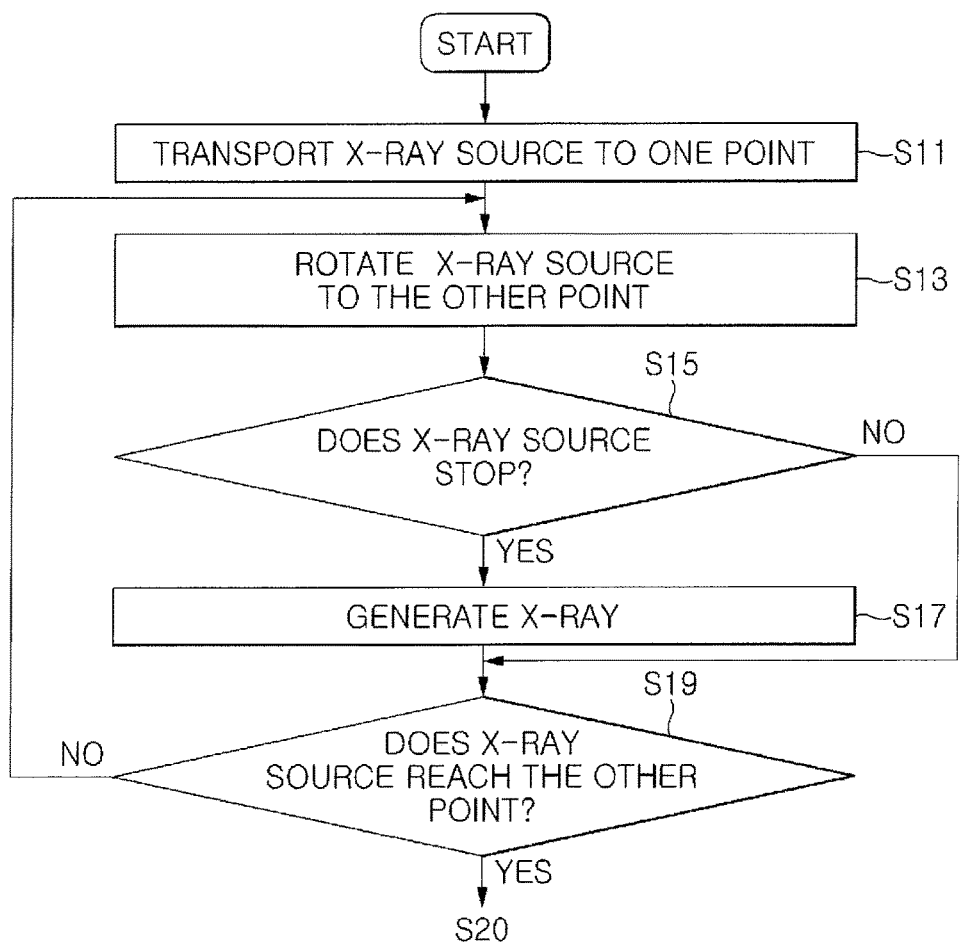
FIG. 28 is a detailed flowchart for S10 of FIG. 11.

FIG. 28 is a detailed flowchart for S10 of FIG. 17.

As illustrated in FIG. 28, a first driving unit 50 transports the X-ray source 10 to one point (P1 of FIG. 6) by a preset angle range in S11.

In S13, the first driving unit 50 rotates the X-ray source 10 from one point by the preset angle range to the other point (P2 of FIG. 7) by a preset angle range.

In S15, the operation control unit 70 verifies whether the X-ray source 10 stops and when the X-ray source 10 stops, the X-ray source 10 generate the X-ray and the generated X-ray is irradiated to the subject in S17 and thereafter, the process proceeds to S19.

Further, the operation control unit 70 verifies whether the X-ray source 10 stops in S15 and when the X-ray source 10 does not stop, the operation control unit 70 verifies whether the X-ray source 10 reaches the other point in S19 and when the X-ray source 10 reaches the other point, the process ends and when the X-ray source 10 does not reach the other point, the process return to S13 again and the first driving unit 50 rotates the X-ray source 10 to the other point.

The apparatus and method for diagnosing lesions according to the present invention are used for digital breast tomosynthesis (DBT) which is a breast cancer diagnosis technique using the 3D image, which can solve problems of mammography which is a breast cancer diagnosis technique using the 2D image in the related art, and in which the 2D images which is a plurality of 2D projected images by the X-ray irradiated at various angles is generated in the X-ray detector 30 by intermittently or continuously rotating the X-ray source 10 by a preset angle range and thereafter, the 3D image is acquired by reconfiguring the 2D images and the acquired 3D image is analyzed to distinguish the presence and location of a lesion without overlapping with a tissue of the subject in a lesion determination unit 40, thereby improving precision in lesion diagnosis.

Further, since the rotational speed of the X-ray source 10 is high as 3□/sec to 5□/sec' (approximately 4.3□/sec) 3°/sec to 5°/sec (approximately 4.3°/sec), rotation of the X-ray source 10 for generating the 2D images may be completed within 10 sec. (approximately 9.73 sec.) even by considering the intermittent rotation of the X-ray source 10, and as a result, a 3D high-resolution image may be generated while a breath of a person to be diagnosed is not instable and X-ray radiation exposure of the subject may be minimized as compared with computerized tomography (CT).

In addition, a first driving pulley 56 that generates driving force of the first driving unit 50 includes a motor and a deceleration gear that is connected with the motor to control the driving force generated from the motor, and since the X-ray source 10 rotates by rotation of a first rotation gear 52, a vibration characteristic and a mechanical driving characteristic of the X-ray source 10 may be enhanced.

Accordingly, the resolution of the 2D images is prevented from being degraded by reducing focus vibration of the X-ray irradiated from the X-ray source 10, the durability and life-span of the apparatus for diagnosing lesions may be increased by low vibration.

While some exemplary embodiments of the present invention have been described with reference to the accompanying drawings, those skilled in the art may change, modify, and substitute the present invention in various ways without departing from the essential characteristic of the present invention. Accordingly, the disclosed exemplary embodiments and the accompanying drawings should not be construed as limiting the technical spirit of the present invention, but the range of the technical spirit of the present invention is not limited by the exemplary embodiments and the accompanying drawings. The protection scope of the present invention should be interpreted based on the following appended claims and it should be appreciated that all technical spirits included within a range equivalent thereto the present invention is included in the appended claims.

The invention claimed is:

1. A method for diagnosing lesions, comprising:
    (a) generating, by an X-ray source, X-rays that irradiate a subject;
    (b) generating 2D images with respect to the subject from the X-rays passing through the subject;
    (c) combining the 2D images to generate a 3D image with respect to the subject; and
    (d) determining the presence or absence of a lesion of the subject by using the 3D image,
    wherein in step (a), the X-ray source rotates intermittently or continuously in accordance with a preset angle range and the generated X-ray irradiates the subject only when the X-ray source stops at a preset angle during intermittent rotation or the generated X-ray irradiates the subject at a preset angle during continuous rotation;
    wherein before step (a), a focus location of the X-ray emitted from the X-ray source is calibrated;
    wherein the calibrating of the focus location of the X-ray emitted from the X-ray source includes:
    (a11) acquiring a plane image for an X-ray passing through a calibration phantom with a plurality of holes;
    (a12) setting a calibration region including a plurality of hole regions formed by the plurality of holes from the acquired plane image; and
    (a13) determining the X-ray focus location by using the plurality of hole regions included in the set calibration region;
    wherein step (a13) includes:
        (a131) determining a hole region most adjacent to each edge of the calibration region among the plurality of hole regions included in the set calibration region and thereafter, calculating a distance from a center point of each determined hole region up to the center of a hole region in which a ratio value of the hole region of the calibration phantom to the area is closest to 1;
        (a132) generating an arc having the center point of each determined hole region as the center and having each calculated distance as a radius on the calibration region;
        (a133) verifying whether coordinates of intersection points of each generated arc are erroneous and thereafter, calculating an average value of the coordinates of the intersection points when the coordinates of the intersection point are not erroneous;
        (a134) repeatedly performing steps (a131) to (a133) with respect to all of the plurality of hole regions included in the calibration region; and
        (a135) calculating an average value of the average values of the coordinate values of the plurality of intersection points calculated in steps (a131) to (a134) and thereafter, finally determining the calculated average value as the X-ray focus location.

2. The method for diagnosing lesions of claim 1, wherein in step (a131), the distance up to the center of a hole region in which a ratio value of the hole region of the calibration phantom to the area is closest to 1 from the center point of the hole region most adjacent to each edge of the calibration region is calculated by an equation below, $$r_i = d \times \left(1 - \frac{A_i}{A_c}\right)$$

wherein, $r_i$ represents a distance up to the center of a hole region in which a ratio value of the hole region of the calibration phantom to the area is closest to 1 from a hole region i, d represents a distance up to the center of the hole region most adjacent to the edge of the calibration region from the center of a hole region in which a ratio value of the hole region of the calibration phantom to the area is closest to 1, $A_i$ represents an area of the hole region i, and $A_c$ represents an area of the hole formed in the calibration phantom.

3. The method for diagnosing lesions of claim 1, wherein in step (a), the X-ray source to rotate by the preset angle range, controls the X-ray source to generate the X-ray to irradiate the subject in accordance with a preset number of irradiation times during the intermittent rotation or controls the X-ray source to generate the X-ray to irradiate the subject at the preset angle in accordance with the preset number of irradiation times during the continuous rotation.

4. The method for diagnosing lesions of claim 1, wherein in step (a), the X-ray source is controlled to rotate in the range of 3°/sec to 5°/sec within the preset angle range.

5. The method for diagnosing lesions of claim 1, wherein in step (d), the subject is a breast of a person to be diagnosed and the lesion is breast cancer.

6. The method for diagnosing lesions of claim 1, wherein in step (a), the preset angle range is −20 degrees to 20 degrees.

7. The method for diagnosing lesions of claim 1, further comprising:
    subsequently to step (a),
    transmitting an X-ray, that has passed through the subject, through a grid positioned below the subject.

8. The method for diagnosing lesions of claim 7, wherein the grid includes a body portion, and a plurality of partitions arranged at a predetermined interval in the body portion, and wherein the X-ray passing through the subject transmits through said body portion.

* * * * *